US 012070265B2

(12) United States Patent
Schweitzer et al.

(10) Patent No.: US 12,070,265 B2
(45) Date of Patent: *Aug. 27, 2024

(54) ELECTROPORATION SYSTEM AND METHOD OF PRECONDITIONING TISSUE FOR ELECTROPORATION THERAPY

(71) Applicant: St. Jude Medical, Cardiology Division, Inc., St. Paul, MN (US)

(72) Inventors: Jeff Schweitzer, St. Paul, MN (US); Gregory K. Olson, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 72 days.

This patent is subject to a terminal disclaimer.

(21) Appl. No.: 17/880,087

(22) Filed: Aug. 3, 2022

(65) Prior Publication Data
US 2022/0370125 A1 Nov. 24, 2022

Related U.S. Application Data

(63) Continuation of application No. 15/947,091, filed on Apr. 6, 2018, now Pat. No. 11,432,871.
(Continued)

(51) Int. Cl.
*A61B 18/12* (2006.01)
*A61B 18/14* (2006.01)
(Continued)

(52) U.S. Cl.
CPC ...... *A61B 18/1492* (2013.01); *A61B 18/1206* (2013.01); *A61B 18/16* (2013.01);
(Continued)

(58) Field of Classification Search
CPC . A61B 18/1492; A61B 18/1206; A61B 18/16; A61B 2018/00636;
(Continued)

(56) References Cited

U.S. PATENT DOCUMENTS 4,838,272 A * 6/1989 Lieber ............... A61N 1/36003
607/48
5,193,537 A 3/1993 Freeman et al.
(Continued)

FOREIGN PATENT DOCUMENTS

AU 2004311842 C1 7/2005
AU 2010214761 B2 12/2012
(Continued)

OTHER PUBLICATIONS

Hunter et al, "Tetanizing pre-pulse: a novel strategy to mitigate ICD shock-related pain", Heart Rhythm, May 2016; 13(5); 1142-1148; accessed at https://www.ncbi.nlm.nih.gov/pmc/articles/PMC4851876/.
(Continued)

*Primary Examiner* — Thomas A Giuliani
(74) *Attorney, Agent, or Firm* — Armstrong Teasdale LLP

(57) ABSTRACT

The present disclosure provides electroporation systems and methods of preconditioning tissue for electroporation therapy. An electroporation generator includes an electroporation circuit, a preconditioning circuit, and a controller. The electroporation circuit is configured to be coupled to a catheter for delivering the electroporation therapy to target tissue of the patient. The electroporation circuit is further configured to transmit an electroporation signal through the catheter. The preconditioning circuit is configured to be coupled to a preconditioning electrode for stimulating skeletal muscle tissue of the patient. The preconditioning circuit is further configured to transmit a preconditioning signal to the preconditioning electrode. The controller is coupled to the electroporation circuit and the preconditioning circuit, and is configured to synchronize transmissions of the electroporation signal and the preconditioning signal such that
(Continued)

the preconditioning signal is transmitted prior to transmission of the electroporation signal.

20 Claims, 4 Drawing Sheets

Related U.S. Application Data

(60) Provisional application No. 62/483,743, filed on Apr. 10, 2017.

(51) Int. Cl.
*A61B 18/16* (2006.01)
*A61N 1/04* (2006.01)
*A61N 1/36* (2006.01)
*A61B 18/00* (2006.01)

(52) U.S. Cl.
CPC ....... *A61N 1/0452* (2013.01); *A61N 1/36042* (2013.01); *A61B 2018/0016* (2013.01); *A61B 2018/00178* (2013.01); *A61B 2018/00351* (2013.01); *A61B 2018/00577* (2013.01); *A61B 2018/00613* (2013.01); *A61B 2018/00839* (2013.01); *A61B 2018/00958* (2013.01); *A61B 2018/1266* (2013.01); *A61B 2018/144* (2013.01); *A61B 2018/165* (2013.01)

(58) Field of Classification Search
CPC .... A61B 2018/0066; A61B 2018/0016; A61B 2018/00351; A61B 2018/00577; A61B 2018/00613; A61B 2018/00839; A61B 2018/00958; A61B 2018/1266; A61B 2018/165; A61B 2018/00642; A61B 2018/00994; A61N 1/0452; A61N 1/327
USPC ...... 606/34, 40, 41, 42, 49; 607/98, 99, 113, 607/115, 116, 119, 122, 123, 129
See application file for complete search history.

(56) References Cited

U.S. PATENT DOCUMENTS

| | | | |
|---|---|---|---|
| 7,937,143 B2* | 5/2011 | Demarais | A61N 1/327 604/501 |
| 8,048,067 B2 | 11/2011 | Davalos et al. | |
| 8,214,033 B2 | 7/2012 | Snell et al. | |
| 8,221,411 B2 | 7/2012 | Francischelli et al. | |
| 8,282,631 B2 | 10/2012 | Davalos et al. | |
| 8,903,488 B2 | 12/2014 | Callas et al. | |
| 9,283,051 B2 | 3/2016 | Garcia et al. | |
| 9,414,881 B2 | 8/2016 | Callas et al. | |
| 9,764,145 B2 | 9/2017 | Callas et al. | |
| 9,788,885 B2 | 10/2017 | Long et al. | |
| 9,987,081 B1 | 6/2018 | Bowers et al. | |
| 10,016,232 B1 | 7/2018 | Bowers et al. | |
| 10,130,819 B2 | 11/2018 | Callas et al. | |
| 10,188,449 B2 | 1/2019 | Gilbert | |
| 10,238,447 B2 | 3/2019 | Neal et al. | |
| 10,271,893 B2 | 4/2019 | Stewart et al. | |
| 10,292,755 B2 | 5/2019 | Arena et al. | |
| 10,342,600 B2 | 7/2019 | Callas et al. | |
| 10,448,989 B2 | 10/2019 | Arena et al. | |
| 10,470,822 B2 | 11/2019 | Garcia et al. | |
| 10,531,914 B2 | 1/2020 | Stewart et al. | |
| 10,722,302 B2 | 7/2020 | Sherman et al. | |
| 10,849,678 B2 | 12/2020 | Onik et al. | |
| 11,432,871 B2* | 9/2022 | Schweitzer | A61N 1/0452 |
| 2004/0236376 A1* | 11/2004 | Miklavcic | A61N 1/325 607/3 |
| 2008/0132884 A1 | 6/2008 | Rubinsky et al. | |
| 2008/0132885 A1 | 6/2008 | Rubinsky et al. | |
| 2012/0116288 A1 | 5/2012 | Miklavcic et al. | |
| 2012/0150169 A1 | 6/2012 | Zielinski et al. | |
| 2013/0218157 A1 | 8/2013 | Callas et al. | |
| 2016/0051324 A1 | 2/2016 | Stewart et al. | |
| 2016/0058493 A1 | 3/2016 | Neal et al. | |
| 2016/0235470 A1 | 8/2016 | Callas et al. | |
| 2016/0331441 A1* | 11/2016 | Konings | A61N 1/327 |
| 2017/0246455 A1 | 8/2017 | Athos et al. | |
| 2017/0319851 A1 | 11/2017 | Athos et al. | |
| 2018/0221078 A1 | 8/2018 | Howard et al. | |
| 2019/0030328 A1 | 1/2019 | Stewart et al. | |
| 2019/0046255 A1 | 2/2019 | Davalos et al. | |
| 2019/0125439 A1 | 5/2019 | Rohl et al. | |
| 2019/0223938 A1 | 7/2019 | Arena et al. | |
| 2019/0233809 A1 | 8/2019 | Neal et al. | |
| 2019/0256839 A1 | 8/2019 | Neal et al. | |
| 2019/0282294 A1 | 9/2019 | Davalos et al. | |
| 2019/0328446 A1 | 10/2019 | Callas et al. | |
| 2019/0350647 A1 | 11/2019 | Ramberg et al. | |
| 2019/0351224 A1 | 11/2019 | Sano et al. | |
| 2019/0376055 A1 | 12/2019 | Davalos et al. | |
| 2020/0093541 A9 | 3/2020 | Neal et al. | |
| 2020/0107879 A1 | 4/2020 | Stewart et al. | |
| 2020/0138506 A1 | 5/2020 | Fraasch et al. | |
| 2020/0147371 A1 | 5/2020 | Pakhomov et al. | |
| 2020/0289188 A1 | 9/2020 | Forsyth et al. | |
| 2020/0289827 A1 | 9/2020 | Forsyth et al. | |
| 2020/0297418 A1 | 9/2020 | Stewart et al. | |
| 2020/0298008 A1 | 9/2020 | Asirvatham | |
| 2020/0315703 A1 | 10/2020 | Sherman et al. | |
| 2020/0405373 A1 | 12/2020 | OBrien et al. | |
| 2021/0015549 A1 | 1/2021 | Haghighi-Mood et al. | |
| 2021/0023362 A1 | 1/2021 | Lorenzo et al. | |

FOREIGN PATENT DOCUMENTS

| | | |
|---|---|---|
| DE | 4191315 T1 | 7/1993 |
| EP | 1395333 A1 | 3/2004 |
| EP | 2425871 A2 | 3/2012 |
| EP | 1696812 B1 | 7/2015 |
| EP | 3232967 A1 | 10/2017 |
| EP | 3573557 A1 | 12/2019 |
| EP | 2736434 B1 | 2/2020 |
| EP | 3614944 A1 | 3/2020 |
| EP | 3624687 A1 | 3/2020 |
| EP | 3749238 A1 | 12/2020 |
| WO | 2019108479 A1 | 6/2019 |
| WO | 2019118436 A1 | 6/2019 |
| WO | 2019157359 A1 | 8/2019 |
| WO | 2020051241 A1 | 3/2020 |
| WO | 2020061192 A1 | 3/2020 |
| WO | 2020198796 A1 | 10/2020 |
| WO | 2020215007 A1 | 10/2020 |

OTHER PUBLICATIONS

International Search Report and Written Opinion for International Patent Application No. PCT/US2018/026444, mailed Jul. 5, 2018, 17 pages.

* cited by examiner

ELECTROPORATION SYSTEM AND METHOD OF PRECONDITIONING TISSUE FOR ELECTROPORATION THERAPY

CROSS REFERENCE OF RELATED APPLICATION

This application is a continuation of U.S. patent application Ser. No. 15/947,091, now U.S. Pat. No. 11,432,871, filed Apr. 6, 2018, which claims priority to U.S. Provisional Application Ser. No. 62/483,743, filed Apr. 10, 2017, both of which are incorporated by reference in their entirety.

FIELD OF DISCLOSURE

The present disclosure relates generally to medical devices that are used in the human body. In particular, in many embodiments, the present disclosure relates to electroporation systems and methods of preconditioning tissue for electroporation therapy.

BACKGROUND

It is generally known that ablation therapy may be used to treat various conditions afflicting the human anatomy. One such condition in which ablation therapy finds a particular application in, for example, is the treatment of atrial arrhythmias. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmia (i.e., irregular heart rhythm) can create a variety of dangerous conditions including loss of synchronous atrioventricular contractions and stasis of blood flow that can lead to a variety of ailments and even death. It is believed that the primary cause of atrial arrhythmia is stray electrical signals within the left or right atrium of the heart. The ablation catheter imparts ablative energy (e.g., radio frequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

One candidate for use in therapy of cardiac arrhythmias is electroporation. Electroporation therapy involves electric field induced pore formation on the cell membrane. The electric field may be induced by applying a direct current (DC) signal delivered as a relatively short duration pulse that may last, for instance, from a nanosecond to several milliseconds. Such a pulse may be repeated to form a pulse train. When such an electric field is applied to tissue in an in vivo setting, the cells in the tissue are subjected to trans-membrane potential, which opens the pores on the cell wall, hence the term electroporation. Electroporation may be reversible (i.e., the temporally-opened pores will reseal) or irreversible (i.e., the pores will remain open). For example, in the field of gene therapy, reversible electroporation (i.e., temporarily open pores) is used to transfect high molecular weight therapeutic vectors into the cells. In other therapeutic applications, a suitably configured pulse train alone may be used to cause cell destruction, for instance by causing irreversible electroporation. Electroporation therapy may also be utilized in other parts of the anatomy.

BRIEF SUMMARY OF THE DISCLOSURE

The present disclosure generally relates to electroporation systems and methods of preconditioning skeletal muscle tissue for electroporation therapy to mitigate undesirable effects of electroporation therapy. Such undesirable effects include skeletal muscle contraction that results from the application of a high-amplitude short-duration DC electrical (IRE) pulse. In many embodiments, the electroporation system includes an electroporation generator having multiple output channels for generating and transmitting electroporation waveforms, i.e., electroporation signals, and one or more preconditioning waveforms, i.e., preconditioning signals. Such electroporation generators deliver current to the patient through pairs of electrodes, including, for example, intracardiac electrodes located on a catheter, and cutaneous electrodes. Alternatively, electroporation may be delivered to other areas of the anatomy. Preconditioning waveforms can be delivered, for example, through one or more pairs of cutaneous electrodes positioned local to regions of skeletal muscle that are desirable to stimulate, such as, for example, and without limitation, the thorax region, arms, and legs of the patient. Alternatively, preconditioning waveforms can be delivered through the catheter that is used to deliver the electroporation therapy. The preconditioning waveforms pre-contract the skeletal muscle to reduce mechanical motion in the patient, affecting a slower, more-controlled, and, notably, weaker skeletal muscle contraction during IRE therapy.

In one embodiment, the present disclosure provides an electroporation generator for delivering electroporation to a patient. The electroporation generator includes an electroporation circuit, a preconditioning circuit, and a controller. The electroporation circuit is configured to be coupled to a catheter for delivering the electroporation therapy to target tissue of the patient. The electroporation circuit is further configured to transmit an electroporation signal through the catheter. The preconditioning circuit is configured to be coupled to a preconditioning electrode for stimulating skeletal muscle tissue of the patient. The preconditioning circuit is further configured to transmit a preconditioning signal to the preconditioning electrode. The controller is coupled to the electroporation circuit and the preconditioning circuit, and is configured to synchronize transmissions of the electroporation signal and the preconditioning signal such that the preconditioning signal is transmitted prior to transmission of the electroporation signal.

In another embodiment, the present disclosure is directed to an electroporation system, including a catheter, a first preconditioning electrode, and an electroporation generator. The catheter includes a distal end configured to be positioned within a patient. The distal end includes a plurality of electrodes configured to deliver an electroporation signal to target tissue within the patient. The first preconditioning electrode is configured to be positioned proximate a first region of skeletal muscle tissue of the patient. The first electrode is configured to deliver a first preconditioning signal to the first region of skeletal muscle tissue. The electroporation generator is coupled to the catheter and the first preconditioning electrode. The electroporation generator is configured to transmit the first preconditioning signal through the first preconditioning electrode, and transmit the electroporation signal through the catheter after transmitting the first preconditioning signal to stimulate the first region of skeletal muscle tissue.

In another embodiment, the present disclosure is directed to a method of delivering electroporation therapy to a patient. The method includes transmitting a first preconditioning signal through a first preconditioning electrode positioned proximate a first region of skeletal muscle tissue of the patient. The first preconditioning signal is configured to stimulate the first region of skeletal muscle tissue for a first preconditioning duration. The method includes transmitting an electroporation signal, after transmitting the first preconditioning signal, through a catheter to a distal end thereof that is positioned within the patient, the electroporation signal configured to deliver electroporation therapy to target tissue of the patient.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
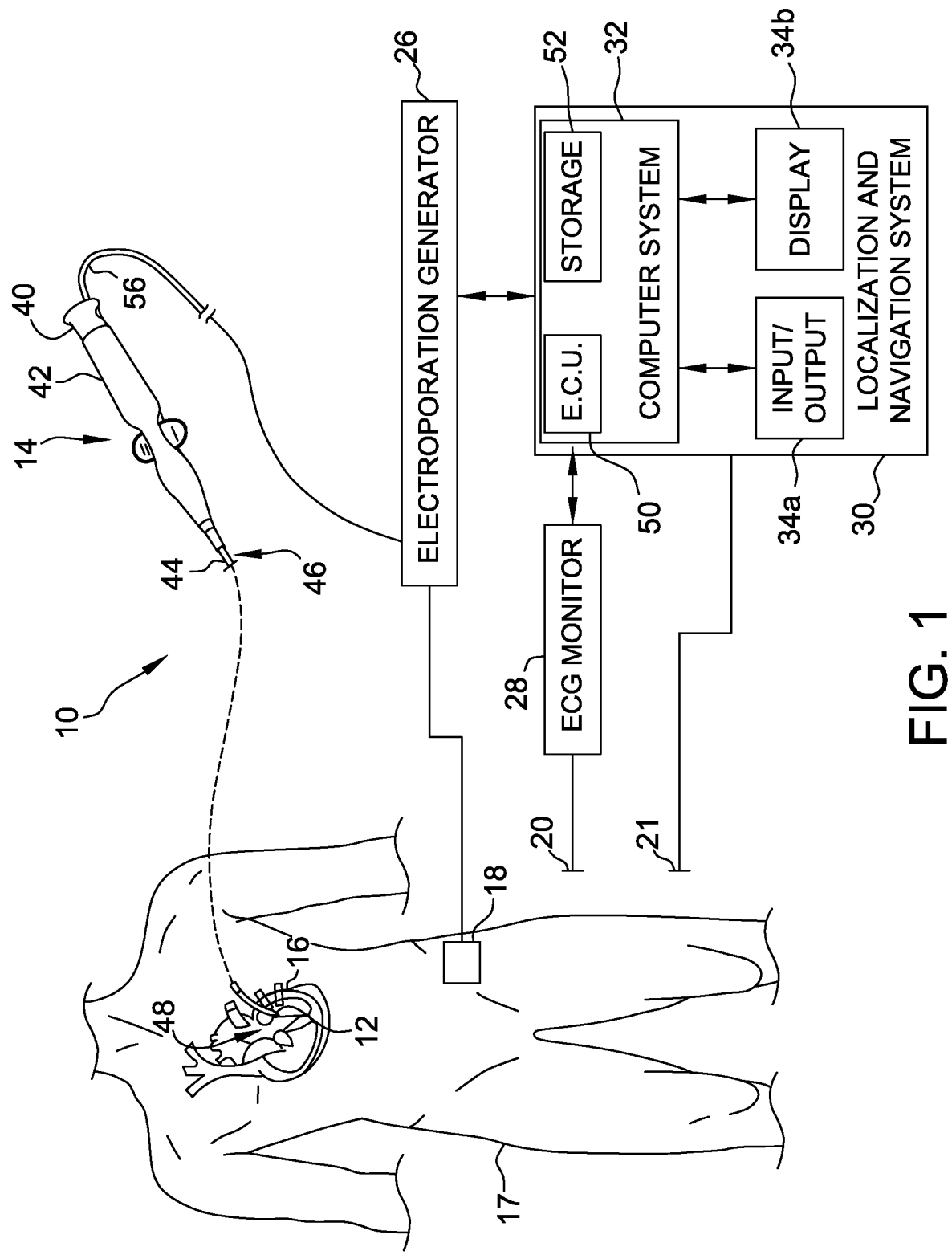
FIG. 1 is a schematic and block diagram view of a system incorporating embodiments for electroporation therapy.

The present disclosure relates generally to medical devices that are used in the human body of a patient. In particular, in many embodiments, the present disclosure relates to electroporation systems and methods of preconditioning tissue for electroporation therapy and, more specifically, irreversible electroporation (IRE). During IRE therapy, a high-amplitude voltage pulse that lasts up to several milliseconds, i.e., the IRE waveform, is applied to target tissue, such as, for example cardiac tissue, to generate the necessary electric field to open the pores of the cardiac cell walls. Such an electric field exhibits a high spatial gradient that compromises the membrane of target cardiac cells and leads to cell destruction. Consequently, the electric field often also stimulates skeletal muscle tissue in a large region of the thorax, resulting in forceful contractions of the skeletal muscle in response to the high-amplitude short-duration DC electrical pulse. It is realized herein that reducing force of skeletal muscle contraction during IRE therapy would improve patients' tolerance of the IRE therapy.

Embodiments of the electroporation systems described herein provide a system for delivering a preconditioning waveform to the skeletal muscle before delivering the IRE waveform to the cardiac tissue to mitigate undesirable effects of electroporation therapy. The IRE waveform is a lower-amplitude electrical signal that "pre-conditions" skeletal muscle to reduce its ability to forcefully contract. Preconditioning waveforms can be any waveform that stimulates skeletal muscle, particularly skeletal muscle in anatomically important regions. Certain regions of skeletal muscle respond to different waveforms in characteristic ways. Generally, the preconditioning waveform pre-contracts the skeletal muscle to reduce mechanical motion in the patient, affecting a slower, more-controlled, and, notably, weaker skeletal muscle contraction during IRE therapy. Preconditioning waveforms may be time-multiplexed for certain regions of skeletal muscle, or, in certain embodiments, applied simultaneously to certain regions of skeletal muscle. Moreover, preconditioning waveforms, in certain embodiments, are applied for various lengths of time. In some embodiments, the electroporation systems described herein include a catheter configured to deliver the preconditioning waveform and the IRE waveform. In other embodiments, the electroporation systems described herein include separate leads, or electrodes, for delivering the preconditioning waveform through a separate path or paths to skeletal muscle, rather than the areas of cardiac tissue targeted during IRE therapy. For example, one or more cutaneous patch electrodes may be used to stimulate, or precondition, one or more areas of skeletal muscle, such as, for example, the thorax region, arm muscles, and leg muscles. In certain embodiments, additional electrodes may be placed at other intracardiac locations to reduce the current flow path through the skeletal muscle, particularly the thorax muscle structures. It is contemplated, however, that the described features and methods of the present disclosure as described herein may be incorporated into any number of systems as would be appreciated by one of ordinary skill in the art based on the disclosure herein.

Figure 2:
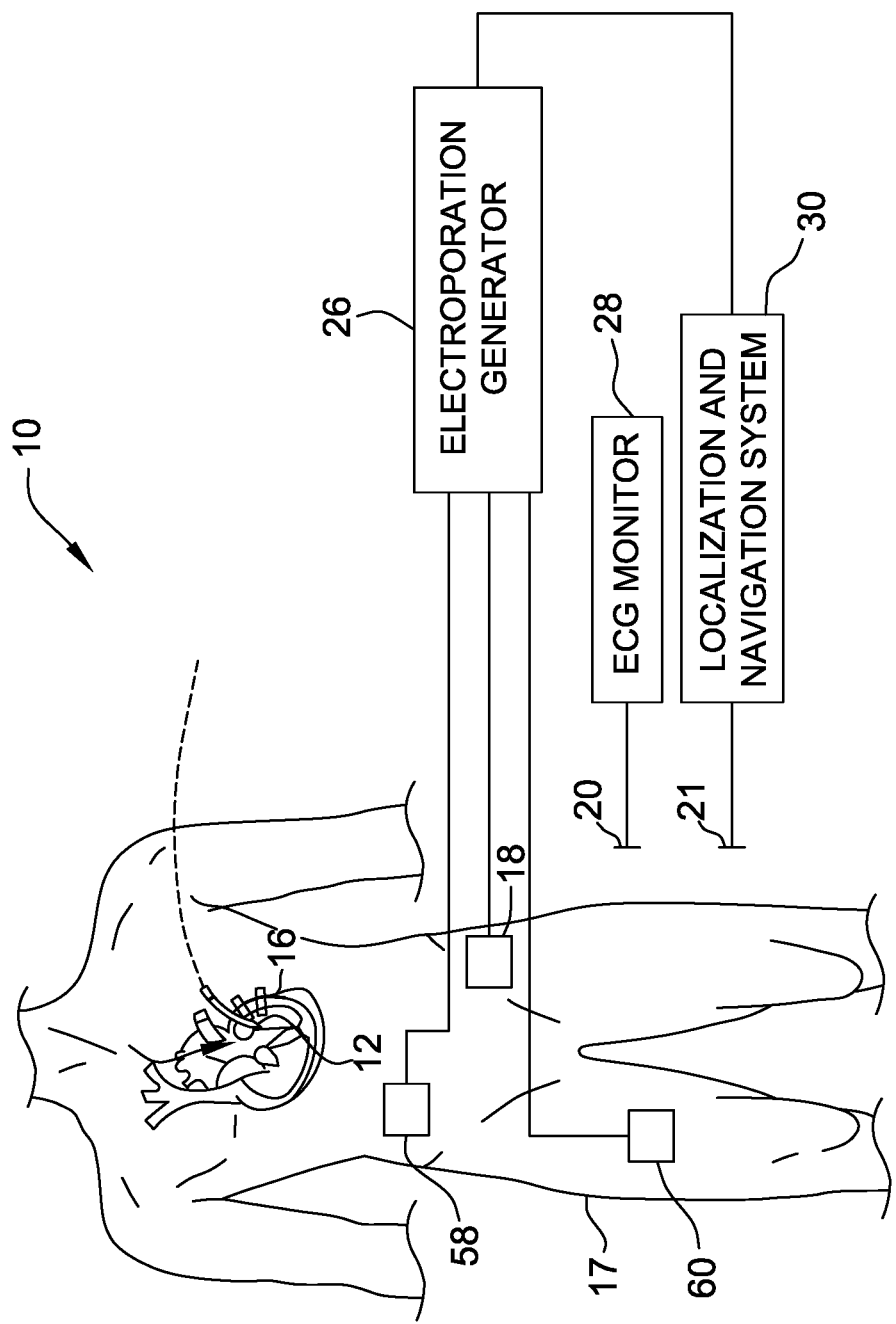
FIG. 2 is a schematic and block diagram view of a system incorporating embodiments for pre-conditioning and electroporation therapy.

Referring now to the drawings, FIG. 1 and FIG. 2 are diagrammatic and block diagram views of a system 10 for electroporation therapy. In general, the various embodiments include an electrode assembly disposed at the distal end of a catheter. As used herein, "proximal" refers to a direction toward the end of the catheter near the clinician and "distal" refers to a direction away from the clinician and (generally) inside the body of a patient. The electrode assembly includes one or more individual, electrically-isolated electrode elements. Each electrode element, also referred to herein as a catheter electrode, is individually wired such that it can be selectively paired or combined with any other electrode element to act as a bipolar or a multi-polar electrode.

System 10 may be used for irreversible electroporation to destroy tissue. In particular, system 10 may be used for electroporation-induced primary necrosis therapy, which refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field in the form of short-duration direct current (DC) pulses (e.g., 0.1 to 20 ms duration) between closely spaced electrodes capable of delivering an electric field strength of about 0.1 to 1.0 kV/cm.

It should be understood that while the energization strategies are described as involving DC pulses, embodiments may use variations and remain within the spirit and scope of the invention. For example, exponentially-decaying pulses, exponentially-increasing pulses, and combinations may be used.

It should be understood that the mechanism of cell destruction in electroporation is not primarily due to heating effects, but rather to cell membrane disruption through application of a high-voltage electric field. Thus, electroporation may avoid some possible thermal effects that may occur when using radio frequency (RF) energy. This "cold therapy" thus has desirable characteristics. Conversely, such an electric field exhibits a high spatial gradient that often also stimulates skeletal muscle tissue in a large region of the thorax, resulting in forceful contractions of the skeletal muscle.

With this background, and now referring again to FIG. 1 and FIG. 2, system 10 includes a catheter electrode assembly 12 including an array of catheter electrodes configured to be used as briefly outlined above and as described in greater detail below. Electrode assembly 12 is incorporated as part of a medical device such as a catheter 14 for electroporation therapy of tissue 16 in a body 17 of a patient. In the illustrative embodiment, tissue 16 comprises heart or cardiac tissue. It should be understood, however, that embodiments may be used to conduct electroporation therapy with respect to a variety of other body tissues.

With continued reference to FIG. 1 and FIG. 2, as noted above, catheter 14 may comprise functionality for electroporation and in certain embodiments also an ablation function (e.g., RF ablation). It should be understood, however, that in those embodiments, variations are possible as to the type of ablation energy provided (e.g., cryoablation, ultrasound, etc.).

In the illustrative embodiment, catheter 14 includes a cable connector or interface 40, a handle 42, and a shaft 44 having a proximal end 46 and a distal end 48. Catheter 14 may also include other conventional components not illustrated herein such as a temperature sensor, additional electrodes, and corresponding conductors or leads. The connector 40 provides mechanical and electrical connection(s) for cable 56 extending from an electroporation generator 26. The connector 40 may comprise conventional components known in the art and as shown is disposed at the proximal end of catheter 14.

Handle 42 provides a location for the clinician to hold catheter 14 and may further provide means for steering or guiding shaft 44 within body 17. For example, handle 42 may include means to change the length of a guidewire extending through catheter 14 to distal end 48 of shaft 44 or means to steer shaft 44 to place electrode assembly 12 in a preferred location and orientation in the anatomy. Moreover, in some embodiments, handle 42 may be configured to vary the shape, size, and/or orientation of a portion of the catheter. For example, where distal end 48 includes a balloon or basket catheter, handle 42 may be configured to transition distal end 48 from a collapsed state to an expanded state. Handle 42 is also conventional in the art and it will be understood that the construction of handle 42 may vary. In an alternate exemplary embodiment, catheter 14 may be robotically driven or controlled. Accordingly, rather than a clinician manipulating a handle to advance/retract and/or steer or guide catheter 14 (and shaft 44 thereof in particular), a robot is used to manipulate catheter 14.

Shaft 44 is an elongated, tubular, flexible member configured for movement within body 17. Shaft 44 is configured to support electrode assembly 12 as well as contain associated conductors, and possibly additional electronics used for selecting electrodes to be energized, signal processing, or conditioning. Shaft 44 may also permit transport, delivery and/or removal of fluids (including irrigation fluids and bodily fluids), medicines, and/or surgical tools or instruments. Shaft 44 may be made from conventional materials such as polyurethane and defines one or more lumens configured to house and/or transport electrical conductors, fluids or surgical tools. Shaft 44 may be introduced into a blood vessel or other structure within body 17 through a conventional introducer. Shaft 44 may then be advanced/retracted and/or steered or guided through body 17 to a desired location such as the site of tissue 16, including through the use of guidewires or other means known in the art.

Shaft 44 houses electrode wires (not shown) for carrying electrical current to the electrodes. Electrode wires extend between handle 42 and the electrodes within an interior portion of shaft 44. To this end, shaft 44 may include an insulator or insulating material. For example, shaft 44 may be packed with an insulation material and/or a cylindrical layer of insulation material may be circumferentially disposed within an interior portion of shaft 44. The thickness and material characteristics of such insulation are selected to configure shaft 44 for safe use with voltage and current in the range of one thousand volts and/or ten amperes.

In some embodiments, catheter 14 is a hoop catheter, sometimes referred to as a spiral catheter, where electrode assembly 12 includes catheter electrodes (not shown) distributed about a structure of one or more hoops at distal end 48 of shaft 44. The diameter of the hoop(s) may vary. In some embodiments, the hoop catheter has a maximum diameter of about twenty-seven millimeters (mm). In some embodiments, the hoop diameter is variable between about fifteen mm and about twenty eight mm. Alternatively, the catheter may be a fixed diameter hoop catheter or may be variable between different diameters. In some embodiments, catheter 14 has fourteen catheter electrodes. In other embodiments, catheter 14 includes ten catheter electrodes, twenty catheter electrodes, or any other suitable number of electrodes for performing electroporation. In some embodiments, the catheter electrodes are ring electrodes. Alternatively, the catheter electrodes may be any other suitable type of electrodes, such as single sided electrode or electrodes printed on a flex material. In various embodiments, the catheter electrodes have lengths of 1.0 mm, 2.0 mm, 2.5 mm, and/or any other suitable length for electroporation.

In some embodiments, catheter 14 is a linear or curvilinear catheter having a linear arrangement of electrodes in electrode assembly 12. Such linear catheters enable a user, in placing catheter 14, to deflect shaft 44 using handle 42. Further, a linear arrangement of electrodes in electrode assembly 12 enables a corresponding linear lesion when energized.

Localization and navigation system 30 may include a visualization system for visualization, mapping, and navigation of internal body structures. System 30 may comprise conventional apparatus known generally in the art (e.g., an EnSite NAVX™ Navigation and Visualization System, commercially available from St. Jude Medical, Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference). It should be understood, however, that this system is exemplary only and not limiting in nature. Other technologies for locating/navigating a catheter in space (and for visualization) are known, including for example, the CARTO navigation and location system of Biosense Webster, Inc., the AURORA® system of Northern Digital Inc., commonly available fluoroscopy systems, or a magnetic location system such as the gMPS system from Mediguide Ltd. In this regard, some of the localization, navigation and/or visualization system would involve a sensor be provided for producing signals indicative of catheter location information, and may include, for example one or more electrodes in the case of an impedance-based localization system, one or more coils (i.e., wire windings) configured to detect one or more characteristics of a magnetic field, for example in the case of a magnetic-field based localization system, or a combination of impedance-based and magnetic-field based localizations systems, such as, for example, the EnSite Precision™ system from St. Jude Medical, Inc.

FIG. 1 and FIG. 2 further show a plurality of return electrodes designated 18, 20, and 21, which are diagrammatic of the body connections, e.g., cutaneous electrodes, that may be used by the various sub-systems included in the overall system 10, such as electroporation generator 26, an electrophysiology (EP) monitor such as an ECG monitor 28, and a localization and navigation system 30 for visualization, mapping and navigation of internal body structures. In the illustrated embodiment, return electrodes 18, 20, and 21 are cutaneous patch electrodes. It should be understood that the illustration of a single cutaneous electrode is diagrammatic only (for clarity) and that such sub-systems to which these patch electrodes are connected may, and typically will, include more than one patch (body surface) electrode. In other embodiments, return electrodes 18, 20, and 21 may be any other type of electrode suitable for use as a return electrode including, for example, the array of catheter electrodes. Return electrodes that are catheter electrodes may be part of electrode assembly 12 or part of a separate catheter (not shown). System 10 may further include a computer system 32 (including an electronic control unit 50 and data storage—memory 52) integrated with localization and navigation system 30 in certain embodiments. Computer system 32 may further include conventional interface components, such as various user input/output mechanisms 34a and a display 34b, among other components.

FIG. 2 further shows a plurality of preconditioning electrodes 58 and 60 electrically coupled to electroporation generator 26. Preconditioning electrodes 58 and 60 are used in combination with electroporation generator 26 to deliver preconditioning waveforms that stimulate one or more regions of skeletal muscle tissue before electroporation therapy is delivered. The illustration of preconditioning electrodes 58 and 60 is diagrammatic only. In certain embodiments, system 10 and electroporation generator 26 may utilize additional preconditioning electrodes. Further, system 10 may utilize return electrodes 18, 20, and 21 to pair with preconditioning electrodes 58 and 60. Alternatively, system 10 may include one or more additional return electrodes (not shown) positioned relative to preconditioning electrodes 58 and 60 such that current paths between preconditioning electrodes 58 and 60 to the return electrodes pass through regions of skeletal muscle tissue that is desired to be stimulated prior to electroporation therapy. Preconditioning electrodes 58 and 60, in the illustrated embodiment, are cutaneous patch electrodes. In some embodiments, electrodes included in electrode assembly 12 at distal end 48 of catheter 14 may be utilized to deliver preconditioning stimulation to certain regions of skeletal muscle tissue.

Electroporation generator 26 is configured to energize the electrode element(s) in accordance with an electroporation energization strategy that may be predetermined or may be user-selectable. For electroporation-induced primary necrosis therapy, generator 26 may be configured to produce an electric current that is delivered via electrode assembly 12 as a pulsed electric field in the form of short-duration DC pulses (e.g., a nanosecond to several milliseconds duration, 0.1 to 20 ms duration, or any duration suitable for electroporation) between closely spaced electrodes capable of delivering an electric field strength (i.e., at the tissue site) of about 0.1 to 1.0 kV/cm. The amplitude and pulse duration needed for irreversible electroporation are inversely related. As pulse durations are decreased, the amplitude is increased to achieve electroporation.

Electroporation generator 26, sometimes referred to herein as a DC energy source, is a monophasic electroporation generator 26 configured to generate a series of DC energy pulses that all produce current in the same direction. In other embodiments, electroporation generator is biphasic or polyphasic electroporation generator configured to produce DC energy pulses that do not all produce current in the same direction. For successful electroporation, some embodiments utilize a two hundred joule output level. Electroporation generator 26 may output a DC pulse having a peak magnitude of between about negative one kilovolt (kV) and about negative two kV at the two hundred joule output level. In some embodiments, electroporation generator 26 outputs a DC pulse having a peak magnitude between about negative 1.5 kV and about negative 2.0 kV. Other embodiments may output any other suitable voltage, including a positive voltage. In some embodiments, electroporation generator 26 is a monophasic defibrillator such as, for example, a Lifepak 9 defibrillator available from Physio-Control, Inc., of Redmond, Washington, USA.

Figure 3:
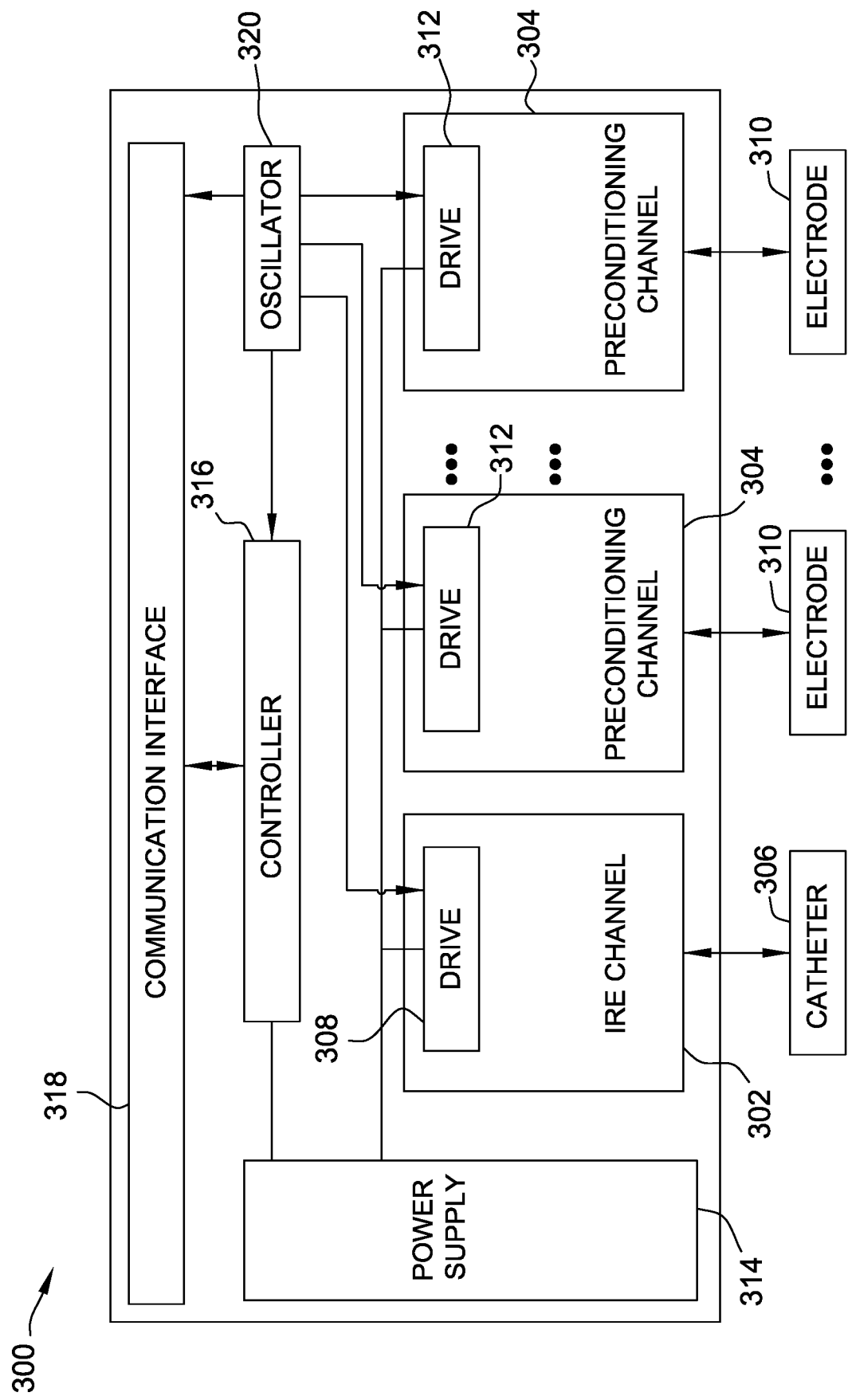
FIG. 3 is a block diagram of an exemplary electroporation generator.

FIG. 3 is a block diagram of an exemplary electroporation generator 300 for use in system 10 (shown in FIG. 1 and FIG. 2). Electroporation generator 300 includes multiple output channels, including an IRE channel 302 and a plurality of precondition channels 304. IRE channel 302 is coupled to a catheter 306, such as catheter 14 (shown in FIG. 1). Catheter 306 generally includes a plurality of catheter electrodes at a distal end for delivering electroporation therapy to target tissue. IRE channel 302 includes a driver 308 for generating the electroporation waveform, i.e., the electroporation signal that is transmitted through catheter 306.

Each precondition channel 304 is configured to be coupled to one or more precondition electrodes 310 that are positioned proximate regions of skeletal muscle tissue to be stimulated during preconditioning. Precondition electrodes 310 may include, for example, cutaneous patch electrodes or catheter electrodes disposed on catheter 306. Each precondition channel 304 includes a driver 312 for generating preconditioning waveforms, i.e., the preconditioning signals that are transmitted through preconditioning electrodes 310. Drivers 312, in certain embodiments, include floating-current-source generators for delivering low-energy preconditioning waveforms to targeted regions of skeletal muscle tissue. Each of drivers 312 may be used to generate distinct preconditioning signals for different and numerous regions of skeletal muscle tissue, which react uniquely to each of the different waveforms. Generally, a preconditioning signal includes any waveform that stimulates tissue and, more preferably, skeletal muscle tissue. Each preconditioning signal may vary in frequency, voltage, current, and duration for which it is transmitted. For example, a first preconditioning signal may be transmitted on a first preconditioning channel at five hertz to deliver ten volt pulses for a duration of up to several seconds; while a second preconditioning signal may be transmitted on a second preconditioning channel at ten hertz to deliver twenty volt pulses for approximately one second. In certain embodiments, multiple preconditioning signals may be multiplexed onto a single preconditioning channel 304 and transmitted through one pair of preconditioning electrodes 310. For example, multiple preconditioning signals may be time multiplexed onto one of preconditioning channels 304. The precise properties of each preconditioning signal are determinable and configurable by electroporation generator 300 based on the region of skeletal muscle tissue that is targeted (and/or the location of one or more cutaneous patches) and the level of stimulation, contraction, and fatigue that is desired prior to delivering electroporation therapy. Electroporation generator 300 may be configured manually by an operator or automatically based on the above-described parameters. For example, in one embodiment, an operator may enter intended cutaneous patch locations into electroporation generator 300, and electroporation generator 300 configures the preconditioning signal based on predetermined properties for the configuration of cutaneous patch locations.

Drivers 308 and 312 are powered by a power supply 314 within electroporation generator 300. Drivers 308 and 312 are also controlled by a controller 316 such that catheter 306 and preconditioning electrodes 310 are energized according to the electroporation strategy set out by the physician, clinician, or other user. Electroporation generator 300 further includes a communication interface 318 for enabling communication among the user and, with reference to FIG. 1 and FIG. 2, localization and navigation system 30. Communication interface 318, in certain embodiments, may include a serial communication channel, fiber communication channel, Ethernet, or any other means for suitably enabling communication among components of system 10.

Electroporation generator 300 also includes an oscillator 320, or other suitable clock or timing device that, in combination with controller 316, synchronizes transmissions of preconditioning signals and electroporation signals. More specifically, preconditioning channels 304 are synchronized to transmit preconditioning signals through preconditioning electrodes 310 for a preconditioning duration before and leading up to transmission of the electroporation signal by IRE channel 302. Notably, the duration for which preconditioning signals are transmitted may be orders-of-magnitude larger than the duration of electroporation therapy itself. Further, the duration that each preconditioning signal is transmitted may vary for the specific region of skeletal muscle tissue that is targeted.

Figure 4:
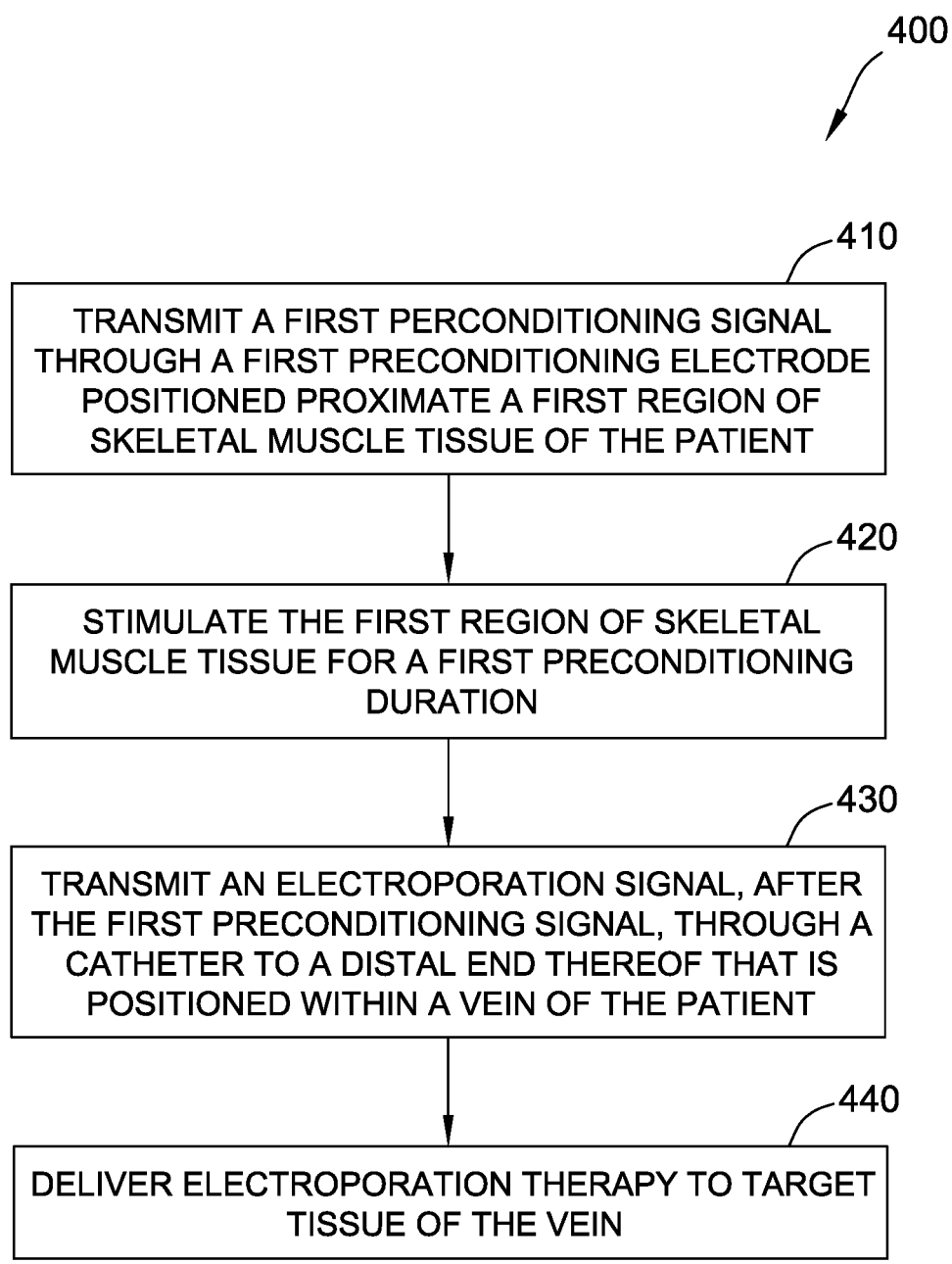
FIG. 4 is a flow diagram of an exemplary method of delivering electroporation therapy to a patient using the systems shown in FIGS. 1-3.

FIG. 4 is a flow diagram of an exemplary method 400 of delivering electroporation therapy to a patient using system 10, shown in FIGS. 1 and 2. System 10 includes electroporation generator 26, which is connected to catheter 14, and cutaneous electrodes 18, 58, and 60. Method 400 includes electroporation generator 26 transmitting 410 a first preconditioning signal through preconditioning electrode 58 positioned proximate a first region of skeletal muscle tissue of the patient's body 17. The first preconditioning signal stimulates 420 the first region of skeletal muscle tissue for a first preconditioning duration.

In certain embodiments, electroporation generator 26 transmits 410 a second preconditioning signal through preconditioning electrode 60 positioned proximate a second region of skeletal muscle tissue of body 17. The second preconditioning signal stimulates 420 the second region of skeletal muscle tissue for a second preconditioning duration.

Transmitting 410 preconditioning signals through preconditioning electrodes 58 and 60 includes forming a current path between each of preconditioning electrodes 58 and 60 and a return electrode, such as, for example return electrode 18. The respective current paths for preconditioning electrodes 58 and 60 pass through the first and second regions of skeletal muscle tissue of body 17.

Electroporation generator 26 synchronizes transmission 410 of the first preconditioning signal such that the preconditioning signal is transmitted 410 before transmitting 430 the electroporation signal through catheter 14 to distal end 48 thereof, which is positioned within, for example, a vein of body 17. The electroporation signal delivers 440 electroporation therapy to target tissue 16 of the body 17 through catheter electrodes located at distal end 48.

The technical effects of the embodiments described above may include: (a) delivering low-energy preconditioning stimulation to one or more region of skeletal muscle tissue prior to delivery of electroporation therapy; (b) stimulating, contracting, or fatiguing skeletal muscle tissue prior to deliver of electroporation therapy through use of preconditioning stimulation; (c) improving control of skeletal muscle contractions before and during electroporation therapy; (d) reducing the force of muscle contractions in patients during electroporation therapy; and (e) improving patients' tolerance of electroporation therapy through use of preconditioning stimulation.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An electroporation generator for delivering electroporation therapy to a patient, the electroporation generator comprising:
   an electroporation circuit configured to be coupled to a catheter for delivering the electroporation therapy to target cardiac tissue of the patient, the electroporation circuit further configured to transmit an electroporation signal through the catheter;
   a stimulation circuit configured to be coupled to a stimulation electrode for stimulating skeletal muscle tissue in a thorax region of the patient that is proximate the target cardiac tissue, the stimulation circuit further configured to transmit a stimulation signal to the stimulation electrode; and
   a controller coupled to the electroporation circuit and the stimulation circuit, the controller configured to synchronize transmissions of the electroporation signal and the stimulation signal, the controller further configured to determine at least one of a frequency or a voltage for the stimulation signal based on the skeletal muscle tissue being located in the thorax region of the patient.

2. The electroporation generator of claim 1, wherein the electroporation circuit is further configured to generate the electroporation signal as a high-voltage direct current (DC) pulse having a pulse width between one and ten milliseconds, inclusively.

3. The electroporation generator of claim 1, wherein the stimulation circuit is further configured to generate the stimulation signal having a voltage between one and twenty volts, inclusively, and at a frequency between one hertz and twenty hertz, inclusively.

4. The electroporation generator of claim 1 further comprising an oscillator coupled to the electroporation circuit, the stimulation circuit, and the controller, the oscillator configured to generate a timing signal, wherein the controller is further configured to initiate transmission of the stimulation signal prior to initiating transmission of the electroporation signal.

5. The electroporation generator of claim 1, wherein the controller is further configured to control the stimulation circuit to transmit the stimulation signal for a duration between one hundred milliseconds and ten seconds, inclusively.

6. The electroporation generator of claim 1 further comprising a second stimulation circuit configured to be coupled to a second stimulation electrode for stimulating a second region of skeletal muscle tissue of the patient, the second stimulation circuit further configured to transmit a second stimulation signal to the second stimulation electrode.

7. The electroporation generator of claim 6, wherein the stimulation signal is a first stimulation signal, and wherein the second stimulation circuit is further configured to generate the second stimulation signal having at least one of a frequency or a voltage that is different than the first stimulation signal.

8. The electroporation generator of claim 1, wherein the stimulation signal is a first stimulation signal, and wherein the stimulation circuit is further configured to transmit a second stimulation signal that is time-multiplexed with the first stimulation signal.

9. An electroporation system comprising:
a catheter having a distal end configured to be positioned in a patient, the distal end having a plurality of electroporation electrodes configured to deliver an electroporation signal to target tissue of the patient;
a first stimulation electrode configured to be positioned proximate a first region of skeletal muscle tissue in a thorax region of the patient, the first stimulation electrode configured to deliver a first stimulation signal to the first region of skeletal muscle tissue to stimulate the first region of skeletal muscle tissue;
an electroporation generator coupled to the catheter and the first stimulation electrode, the electroporation generator configured to transmit the first stimulation signal through the first stimulation electrode, and transmit the electroporation signal through the catheter, wherein the electroporation generator is further configured to determine at least one of a frequency or a voltage for the first stimulation signal based on the first region of skeletal muscle tissue being located in the thorax region of the patient.

10. The electroporation system of claim 9, wherein the first stimulation electrode is a cutaneous patch electrode.

11. The electroporation system of claim 9 further comprising a return electrode configured to be positioned relative to the first stimulation electrode such that an electrical pathway therebetween passes through the first region of skeletal muscle tissue.

12. The electroporation system of claim 9 further comprising a second stimulation electrode coupled to the electroporation generator and configured to be positioned proximate a second region of skeletal muscle tissue of the patient, the second electrode configured to deliver a second stimulation signal to the second region of skeletal muscle tissue, wherein the electroporation generator is further configured to transmit the second stimulation signal through the second stimulation electrode.

13. The electroporation system of claim 12, wherein the first stimulation signal is different from the second stimulation signal.

14. The electroporation system of claim 9, wherein the first stimulation electrode is disposed on the distal end of the catheter.

15. A method of delivering electroporation therapy to a patient, the method comprising:
determining, using an electroporation generator, at least one of a frequency or a voltage for a first stimulation signal based on a target of the first stimulation signal being located in a thorax region of the patient;
transmitting the first stimulation signal through a first stimulation electrode positioned proximate a first region of skeletal muscle tissue in the thorax region of the patient that is proximate target cardiac tissue of the patient, the first stimulation signal configured to stimulate the first region of skeletal muscle tissue for a first stimulation duration; and
transmitting an electroporation signal through a catheter to a distal end of the catheter, the catheter positioned within the patient, the electroporation signal configured to deliver electroporation therapy to the target cardiac tissue of the patient.

16. The method of claim 15 further comprising:
positioning the first stimulation electrode proximate the first region of skeletal muscle tissue; and
positioning a ground electrode relative to the first stimulation electrode such that an electrical pathway therebetween passes through the first region of skeletal muscle tissue.

17. The method of claim 15 further comprising transmitting a second stimulation signal through a second stimulation electrode positioned proximate a second region of skeletal muscle tissue of the patient, the second stimulation signal configured to stimulate the second region of skeletal muscle tissue for a second stimulation duration.

18. The method of claim 15 further comprising generating the first stimulation signal at a frequency between one hertz and twenty hertz.

19. The method of claim 15, wherein transmitting the first stimulation signal comprises transmitting the first stimulation signal through the catheter to the first stimulation electrode disposed on the distal end of the catheter.

20. The method of claim 15, wherein transmitting the first stimulation signal comprises transmitting the first stimulation signal prior to transmitting the electroporation signal.

* * * * *